United States Patent [19]

Giraud et al.

[11] Patent Number: 5,463,120

[45] Date of Patent: Oct. 31, 1995

[54] METHOD FOR THE CRYSTALLIZATION OF METHIONINE

[75] Inventors: Jean Giraud, Salindres; Daniel LeClaire, Durdat Larequille, both of France

[73] Assignee: Rhone-Poulenc Nutrition Animale, Antony, France

[21] Appl. No.: 279,164

[22] Filed: Jul. 22, 1994

[30] Foreign Application Priority Data

Jul. 28, 1993 [FR] France .................................. 93 09273

[51] Int. Cl.$^6$ .................................................. C07C 321/00
[52] U.S. Cl. ............................................ 562/559; 562/554
[58] Field of Search .................................... 562/559, 554

[56] References Cited

FOREIGN PATENT DOCUMENTS 43-22285  9/1943  Japan .
43-24890  10/1943  Japan .
46-19610  6/1971  Japan .

OTHER PUBLICATIONS

"Recrystallization of DL–methionine", Sawaki et al., Chemical Abstracts, abstract No. 39393w, 71(9) :346 (1969).

*Primary Examiner*—Michael L. Shippen
*Attorney, Agent, or Firm*—Finnegan, Henderson, Farabow, Garrett & Dunner

[57] ABSTRACT

A process for the crystallization of DL-methionine from a crystallization medium comprising DL-methionine and an aluminium salt of an organic acid.

18 Claims, No Drawings

METHOD FOR THE CRYSTALLIZATION OF METHIONINE

The present invention relates to a new process for the crystallization of DL-methionine. The present invention more particularly relates to an improved process for the crystallization of DL-methionine by addition, prior to the crystallization, of a crystallization additive to the solution containing the methionine.

It is known, according to Japanese Patent published under number JP 68-024890, that it is possible to improve the crystallization of methionine by the addition of alcohols, phenols or ketones having 4 to 18 carbon atoms. It is also known, according to Japanese Patent published under number 71-019610, that it is possible to crystallize methionine by the addition of an anionic or non-ionic surface-active agent to the medium in which the methionine is soluble. It is further known, according to Japanese Patent published under number 68-022285, that it is alternatively possible to crystallize methionine from solutions containing methionine by the addition of water-soluble cellulose derivatives.

The present invention has made it possible to improve the crystallization of methionine from the neutralization solution of sodium methioninate while avoiding the formation of amorphous, and therefore dusty, products.

A process of the present invention for the crystallization of DL-methionine comprises the step of crystallizing DL-methionine from a crystallization medium (solution), preferably an aqueous solution, comprising DL-methionine and an aluminium salt of an organic acid, preferably a water soluble aluminum salt of an organic acid, to form crystals of DL-methionine.

The crystallization additive is chosen from water-soluble salts of aluminium and of an organic acid. The organic acid is preferably soluble in water and preferably contains at most 8 carbon atoms and, still more preferably, at most 4 carbon atoms. The organic acid further preferably contains one or more alcohol and/or acid functional groups.

Mention may be made, without implied limitation, of the following acids which are suitable acids for use in the process of the invention:

lactic acid glycolic acid acetic acid malic acid tartaric acid citric acid.

The use of lactic acid, glycolic acid and acetic acid to form aluminium lactate, glycolate and acetate, respectively, is very particularly preferred.

The salts of organic acids and of aluminium have the advantage, with respect to the salts of aluminium and of inorganic acids, of being able to be used at a pH of between 4.5 and 7 and preferably between 4.5 and 5.5 without the concomitant precipitation of aluminium hydroxide.

The present invention makes it possible to directly crystallize methionine from a solution (crystallization medium) containing methionine and sodium sulphate, the pH of which is approximately 5, to which is added a sufficient amount of an aluminium salt of an organic acid.

This solution, containing methionine and sodium sulphate, results from the acidification, by sulphuric acid, of a solution containing sodium methioninate and sodium carbonate, which solution results from the hydrolysis of the hydantoin.

The addition of an organic aluminium salt to the sodium sulphate and methionine solution, preferably accompanied by cooling of the crystallization medium to approximately 40° C., makes it possible to obtain methionine crystals without the significant appearance of cloudiness which is caused by aluminium hydroxide, and without a filtration problem during the isolation of the methionine crystals.

The amount, by weight, of organic aluminium salt added to or otherwise present in the crystallization medium, expressed as an aluminium equivalent calculated with respect to the methionine, is preferably between 500 and 5000 ppm, and more preferably between 500 and 3000 ppm.

In the case of aluminium lactate, the amount added during the crystallization process can advantageously vary within wide limits without influencing the subsequent filtration whereas, when aluminium sulphate is used, increasing the amount of aluminium can cause problems during filtration. Thus, the use of aluminium lactate advantageously makes possible successive recyclings of the filtration mother liquors, which may not be possible when aluminium sulphate is used. The amount of lactate used will be adapted, by those skilled in the art, to the economics of the process; it is obvious that excessively high amounts beyond 5000 ppm do not introduce any additional technical advantage and irretrievably burden the economics of the process.

The organic aluminium salt can be used alone or by combining two or more different salts.

The crystalline methionine obtained can be recovered by any suitable separation method, such as filtration or centrifugation. The crystals obtained can contain less water than those obtained in the absence of an additive. The crystals obtained can have the form of grains and can have a density of approximately 0.50, which is a much higher density than that of methionine crystals obtained without additive.

The present invention will be more completely described using the following examples which should not be regarded as limiting the invention.

EXAMPLE 1

0.327 g of aluminium lactate, as a 20% solution in water, was added to a 1-liter receptacle which contained 650 g of an aqueous solution. The aqueous solution, containing 60 g of DL-methionine and 98.1 g of sodium sulphate, was maintained at 100° C. The pH of the aqueous solution was 5.

The crystallization medium was slowly cooled to 40° C. while stirring was continued at 300 revolutions/minute. 39.1 g of DL-methionine crystals were recovered; the characteristics of the crystals are shown in Table 1.

EXAMPLES 2 AND 3

Example 1 was reproduced, wherein aluminium lactate was replaced by respectively, 0.132 g of aluminium acetate in Example 2, and 0.28 g of aluminium glycolate in Example 3. Both the aluminium acetate and aluminium glycolate were employed as 15% solutions in water. The results are shown in Table 1.

EXAMPLES 4 TO 7

1000 to 3000 ppm, with respect to the amount of methionine, of aluminium in either the lactate or the sulphate form, was added to a neutralized solution from the saponification of the hydantoin, which contained 9.2% by weight of methionine and 15% by weight of sodium sulphate. This mixture was maintained at 100° C. at atmospheric pressure and had a pH between 5 and 5.5.

The presence or the absence of the formation of a precipitate was observed. The results demonstrate that the aluminium lactate, compared to the sulphate, can be used at different concentrations and different pH levels without causing filtration problems.

TABLE 1

| Test | Additives | Al level (ppm)/MTN | Loss on drying (%) | Density | Appearance of the crystals |
|---|---|---|---|---|---|
|  | without (control) | 0 | 35.2 | 0.27 | amorphous lamellae |
| 1 | Lactate | 500 | 25 | 0.52 | small grains |
| 2 | Acetate | 500 | 22.2 | 0.55 | small grains |
| 3 | Glycolate | 500 | 27.9 | 0.51 | small grains |

TABLE 2

| Test | pH | Al Level (ppm)/MTN | Additive | Solution | Filtration |
|---|---|---|---|---|---|
| C4 | 5 | 3000 | Sulphate | Cloudy | slow + foam |
| 4 | 5 | 3000 | Lactate | Clear | normal |
| C5 | 5 | 2000 | Sulphate | Cloudy | slow (30 min) |
| 5 | 5 | 2000 | Lactate | Clear | normal |
| C6 | 5.5 | 3000 | Sulphate | Cloudy | very difficult (2h 30) |
| 6 | 5.5 | 3000 | Lactate | Clear | normal |
| C7 | 5.5 | 1000 | Sulphate | Cloudy | normal |
| 7 | 5.5 | 1000 | Lactate | Clear | normal |

What is claimed is:

1. A process for the crystallization of DL-methionine comprising the step of crystallizing DL-methionine from a crystallization medium comprising DL-methionine and a water soluble aluminium salt of an organic acid to form crystals of DL-methionine.

2. A process according to claim 1, wherein the organic acid is soluble in water.

3. A process according to claim 1, wherein the organic acid contains at most 8 carbon atoms.

4. A process according to claim 3, wherein the organic acid contains at most 4 carbons.

5. A process according to claim 1, wherein the organic acid is an acid alcohol.

6. A process according to claim 1, wherein the organic acid is a polycarboxylic acid.

7. A process according to claim 1, wherein the organic acid is selected from lactic acid, glycolic acid and acetic acid.

8. A process according to claim 1, wherein the amount by weight of said aluminium salt of the organic acid, expressed as an aluminium equivalent calculated with respect to the methionine, is between 500 and 5000 ppm.

9. A process according to claim 8, wherein the amount by weight of aluminium salt of the organic acid, expressed as an aluminium equivalent calculated with respect to the methionine, is between 500 and 3000 ppm.

10. A process according to claim 1, wherein the pH of the crystallization medium is between 4.5 and 7.

11. A process according to claim 10, wherein the pH of the crystallization medium is between 4.5 and 5.5.

12. A process according to claim 1, wherein the crystallization medium is an aqueous solution comprising said aluminium salt, said DL-methionine and sodium sulphate.

13. A process according to claim 12, wherein the pH of the aqueous solution is about 5.

14. A process according to claim 1, wherein the crystallization medium is formed by adding said aluminium salt to an aqueous solution comprising DL-methionine and sodium sulphate, and further comprising the step of cooling said crystallization medium, after the addition of said aluminum salt, to a temperature of about 40° C.

15. A process according to claim 1, wherein said crystallization medium is an aqueous solution.

16. A process according to claim 1, wherein said organic acid is lactic acid.

17. A process according to claim 9, wherein the amount by weight of said aluminium salt is 500 ppm.

18. A process according to claim 16, wherein the amount of said aluminium salt is between 1000 ppm and 3000 ppm.

* * * * *